United States Patent [19]

Neuenschwander et al.

[11] Patent Number: 5,319,059
[45] Date of Patent: Jun. 7, 1994

[54] PLASTIC X-RAY CONTRAST MATERIAL

[75] Inventors: Peter Neuenschwander, Baden; Falah Redha, Ortschwaben; Ulrich W. Suter; Georg Uhlschmid, both of Zurich, all of Switzerland

[73] Assignee: Juliane Jeck, Fed. Rep. of Germany

[21] Appl. No.: 956,881

[22] PCT Filed: Apr. 10, 1992

[86] PCT No.: PCT/DE92/00294
§ 371 Date: Dec. 11, 1992
§ 102(e) Date: Dec. 11, 1992

[87] PCT Pub. No.: WO92/18167
PCT Pub. Date: Oct. 29, 1992

[30] Foreign Application Priority Data

Apr. 12, 1991 [DE] Fed. Rep. of Germany ....... 4111914

[51] Int. Cl.$^5$ ............................................. C08L 75/04
[52] U.S. Cl. ..................................... 528/73; 528/74.5; 528/76; 528/80; 528/83; 528/85
[58] Field of Search ..................... 528/73, 74.5, 76, 80, 528/83, 85

[56] References Cited

U.S. PATENT DOCUMENTS 3,852,341 12/1974 Bjork et al. ........................... 528/80
4,283,447 8/1981 Flynn .................................... 528/52
4,406,878 9/1983 DeBoer ................................. 528/44

FOREIGN PATENT DOCUMENTS 0203833 3/1986 European Pat. Off. .
8707155 12/1987 PCT Int'l Appl. .
8806162 8/1988 PCT Int'l Appl. .

OTHER PUBLICATIONS

Lipatova, T. E., "Some Chemical Aspects of the Behavior of Synthetic Polymers in a Living Organism", Journal of Polymer Science: Polymer Symposium 66, pp. 239–257 (1979).

Masar, B., et al., "Synthesis of Polyurethanes and Investigation of their Hydrolytic Stability", Journal of Polymer Science: Polymer Symposium 66, 259–268 (1979), John Wiley & Sons, Inc.

Houben–Weyl, Methoden der organischen Chemie (Methods of Organic Chemistry), vol. E 20, Makromol. Stoffe (Macromolecular Materials), pp. 1719 to 1721 (1987).

Primary Examiner—Maurice J. Welsh
Attorney, Agent, or Firm—Speckman, Pauley & Fejer

[57] ABSTRACT

A material of polyurethane with covalently linked X-ray contrast material, where the polyurethane is biocompatible, stable or also biodegradable in an appropriate environment, as well as X-ray contrasting.

22 Claims, No Drawings

PLASTIC X-RAY CONTRAST MATERIAL

BACKGROUND OF THE INVENTION

1. Field of the Invention

This invention relates to a plastic material which is opaque to X-rays, in particular, polyurethane having a covalently linked X-ray contrast material.

2. Description of the Prior Art

Use of plastics in industry, agriculture, medicine or other applications is often tied to the question of locating and testing the material during its use. In addition in medical applications it must not only be possible to locate the implanted or applied plastics, but also the plastics must be removable from the human or animal body after a set period of time. As a rule, removal requires a further surgical procedure. Although easily locatable plastics are known, they are chemically stable and can only be removed from the human body by a surgical procedure. On the other hand, plastics are known which degrade and are removed from the body after a certain time when their purpose has been served. However, such plastics are not easy to locate.

A polyurethane which is opaque to X-rays but which is not has been disclosed biologically degradable in Derwent Abstract 87-348546/49 of WO 8707-155 which, however, is not biologically degradable. However if it were biologically degradable, highly toxic halogen derivates of isophtalic acid would be created, as a result of which the polymer would not be biocompatible. Biocompatible and/or biodegradable polyurethanes which, however, are not X-ray contrasting, have been disclosed in J. Polym. Sci., Polym. Symp. 66, pp. 259 to 268 (1979) or J. Polym. Sci., Polym. Symp. 66, pp. 239 to 257 (1979), as well as in Houben-Weyl, Methoden der organischen Chemie [Methods of Organic Chemistry], Volume E 20, Makromol. Stoffe [Macromolecular Materials], pp. 1719 to 1721 (1987).

SUMMARY OF THE INVENTION

Accordingly, it is an object of this invention to provide a material which, can be located with a high degree of accuracy and which can also be dissolved in the human or animal body.

This object is attained by a material of polyurethane with a covalently linked X-ray contrast material in accordance with one embodiment of this invention comprising a polyurethane which is biocompatible, stable or biodegradable in an appropriate environment, and X-ray contrasting.

DESCRIPTION OF PREFERRED EMBODIMENTS

Polyurethanes impervious to X-rays are particularly suited for temporary or permanent use of in connection with X-ray identification. In the solid aggregate state, devices, structures, films, foils, tubes, hoses, screws, rods or other three-dimensional compact or hollow structures are made from polyurethanes in addition the polyurethane in case is also suitable for coatings of the structures, insulation, seals and as a drug carrier. In the liquid aggregate state, the polyurethane can be used for filling empty or filled biological or technical hollow spaces and/or for diagnostic, medical or technical purposes. Furthermore, the polyurethane can be used for the additional purpose of X-ray identification. The polyurethane can also be employed in the form of sprays, dispersions or as a dispersion medium. Work pieces can be coated with this polyurethane, but topical application is also not excluded. Hardening by application of external energy is used for this application.

For example blockage of the exocrinal duct system of the pancreas by injection of the dissolved plastic through a catheter is a surgical procedure which may be required during transplantation of this organ.

From a medical viewpoint, the plastic to be used for this purpose requires specific properties, including:

a. Biocompatibility b. Solubility in solvents which are only weakly or not toxic, such as alcohol, dimethylsulfoxide, DIM or their mixtures, c. Insolubility in an aqueous environment (water, blood, etc.)

d. Solid, resilient or visco-resilient behavior following precipitation, e. Ability to decompose biologically, and f. X-ray absorbency to a sufficient and variable extent.

In particular, polyurethanes are suitable in which one of their two basic compounds, in this case the diol compound, is entirely or partially replaced by the glycerine monoester of diatrizoic acid (1) or by the glycerine monoester of a triiodobenzoic acid derivative (2, 3, 4, 5) or by an iodinated pyridone-4 derivative, for example iopydol (6).

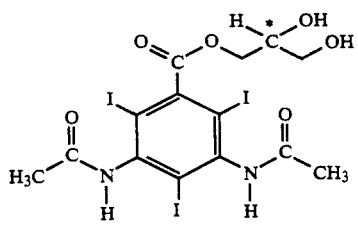

1)

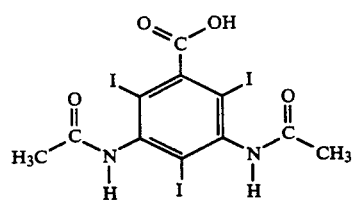

2)

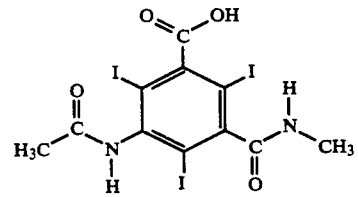

3)

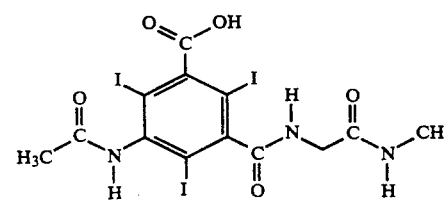

4)

The following diols are used as co-condensable diol compounds:

a. Bi-valent alcohols of the type

HO—(CH$_2$)$_n$—OH  n = 2-12 b. Polyether diols of the type

HO—[(CH$_2$)$_m$—O]$_n$—[(CH$_2$—CH(CH$_3$)—O)$_p$]—H m = 2-6  n,p = 0-20 c. Polyester diols on the basis of
I. Adipic acid/ethylene glycol-co-propylene glycol
   Adipic acid/ethylene glycol
   Adipic acid/propylene glycol
II. Polyglycol diol and polyglycol-co-lactide-diol
IV. Poly-3-hydroxy-butyric acid diol and poly-3-hydroxy-butyric acid-co-3-hydroxy valeric acid diol
V. Poly-3-hydroxy valeric acid diol
VI. Poly-caprolactone diol
VII. De-polymerized cellulose
VIII. De-polymerized cellulose acetate The polyester diols on the basis of II to V are produced by transesterification of higher-molecular polyesters with ethylene glycol, diethylene glycol and triethylene glycol with simultaneous cleavage into macrodiols having mean molecular weights between $M_n$ 500 and 10000.

The following compounds can be used as diisocyanates:
1. 5-isocyanato-1-(isocyanatomethyl)-1, 3, 3-trimethylcyclohexane (isophorone diisocyanate) (IDPI)
2. 1, 3-bis(1-isocyanato-1-methyl)-benzene (TMXDI)
3. Hexamethylene diisocyanate (HDI)
4. 2, 2, 4-trimethyl-hexamethylene diisocyanate (THDI)

Condensation of the compounds occurs in solution in a mixture of dioxane/dimethylformamide having a mixing ratio between 1:1 to 20:1 at temperatures between 40° and 100° C., with or without a catalyst. Isolation of the polymers is accomplished by precipitation in water. Purification is accomplished by repeated dissolution of the polymer and precipitation in water.

The polymer made from the above described compounds is represented by way of example by the following formula:

where $x \geq 1$, $y \leq 1000$ and $1 \leq n \leq 50$

We claim:

1. In a material of polyurethane to which an X-ray contrast material is covalently bonded, forming a plastic, the improvement comprising:
   the polyurethane being biocompatible, one of stable and biodegradable, and X-ray contrasting.

2. A material in accordance with claim 1, wherein the plastic is soluble in one of non-toxic and weakly toxic solvents.

3. A material in accordance with claim 1, wherein the plastic is insoluble in an aqueous environment.

4. A material in accordance with claim 1, wherein the plastic is one of solid and viscoelastic.

5. A material in accordance with claim 1, wherein one of two precursor compounds for forming said polyurethane is at least partially replaced by a compound selected from the group consisting of a glycerine monoester of diatrizoic acid (1), a glycerine monoester of a triiodobenzoic acid derivative (2, 3, 4, 5) and an iodinated pyridon-4 derivative (6):

4) 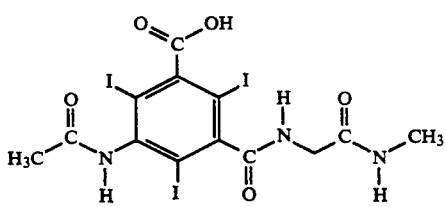

5) 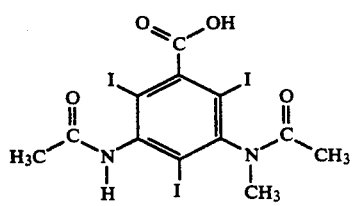

6) 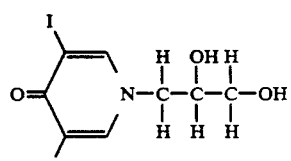

6. A material in accordance with claim 1, wherein at least one diol selected from the group consisting of:
  a. Bi-valent alcohols of the type HO—(CH₂)ₙOH  n=2–12 b. Polyether diols of the type

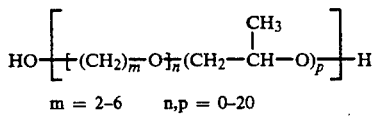

m = 2–6   n,p = 0–20 c. Polyester diols on the basis of
  I. Adipic acid/ethylene glycol-co-propylene glycol Adipic acid/ethylene glycol Adipic acid/propylene glycol
  II. Polyglycol diol and polyglycol-co-lactide-diol
  IV. Poly-3-hydroxy-butyric acid diol and poly-3-hydroxy-butyric acid-co-3-hydroxy valeric acid diol
  V. Poly-3-hydroxy valeric acid diol
  VI. Poly-caprolactone diol
  VII. De-polymerized cellulose
  VIII. De-polymerized cellulose acetate is used as a co-condensible diol compound.

7. A material in accordance with claim 6, wherein the polyester diols on the basis of II, IV and V are produced by transesterification of higher-molecular polyesters with ethylene glycol, diethylene glycol and triethylene glycol with simultaneous cleavage into a plurality of macro-diols having a mean molecular weight between about $M_n$ 500 and 10000.

8. A material in accordance with claim 1, wherein a diisocyanate is selected from the group consisting of:
  1. 5-isocyanato-1-(isocyanatomethyl)-1,3,3-trimethyl-cyclohexane (isophorone diisocyanate) (IDPI)
  2. 1,3-bis(1-isocyanato-1-methyl)-benzene (TMXDI)
  3. Hexamathylene diisocyanate (HDI)
  4. 2,2,4-trimethyl-hexamethylene diisocyanate (THDI).

9. A material in accordance with claim 1, wherein condensation of the compounds occurs in a solution in a mixture of dioxane/dimethylformamide with a mixing ratio between 1:1 to 20:1 at a temperature between about 40° C. and about 100° C.

10. A material in accordance with claim 1, wherein isolation of the polymers is accomplished by precipitation in water.

11. A material in accordance with claim 1, wherein purification is accomplished by repeated dissolution of the polymer and precipitation in water.

12. A material in accordance with claim 1, wherein said polymer is represented by the formula:

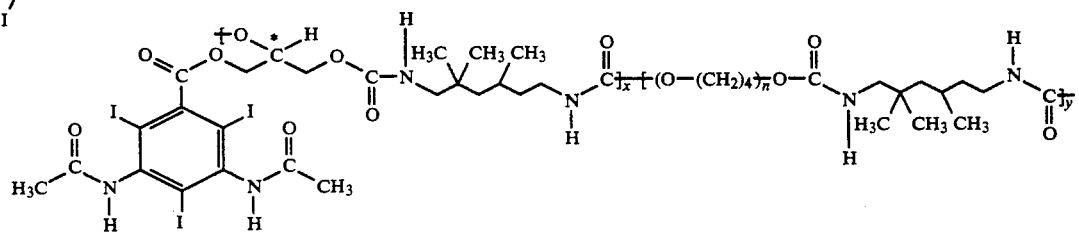

where $x \geq 1$, $y \leq 1000$ and $1 \leq n \leq 50$.

13. A material in accordance with claim 2, wherein the plastic is insoluble in an aqueous environment.

14. A material in accordance with claim 13, wherein the plastic is one of solid and viscoelastic.

15. A material in accordance with claim 14, wherein one of two precursor compounds for forming said polyurethane is at least partially replaced by a compound selected from the group consisting of a glycerine monoester of diatrizoic acid (1), a glycerine monoester of a triiodobenzoic acid derivative (2, 3, 4, 5) and an iodinated pyridon-4 derivative (6):

1) 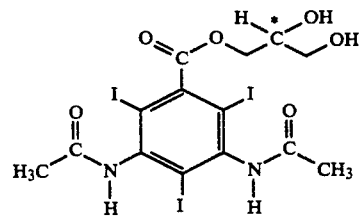

2) 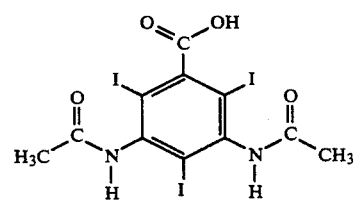

3)

[structure: triiodobenzene with COOH, NHC(O)CH3, and C(O)NHCH3 substituents]

4)

[structure: triiodobenzene with COOH, NHC(O)CH3, and C(O)NHCH2C(O)NHCH3 substituents]

5)

[structure: triiodobenzene with COOH, two NC(O)CH3 groups, one with N-CH3]

6)

[structure: iodinated compound with N-C(H)-C(OH)(H)-C(H)-OH chain]

16. A material in accordance with claim 15, wherein at least one diol selected from the group consisting of:

a. Bi-valent alcohols of the type

HO—(CH$_2$)$_n$OH  n=2–12 b. Polyether diols of the type $$HO-[-(CH_2)_{\overline{m}}-O-]_{\overline{n}}(CH_2-\underset{\underset{CH_3}{|}}{CH}-O)_{\overline{p}}-H$$

m = 2–6    n,p = 0–20 c. Polyester diols on the basis of
 I. Adipic acid/ethylene glycol-co-propylene glycol Adipic acid/ethylene glycol Adipic acid/propylene glycol
 II. Polyglycol diol and polyglycol-co-lactide-diol
 IV. Poly-3-hydroxy-butyric acid diol and poly-3-hydroxy-butyric acid-co-3-hydroxy valeric acid diol
 V. Poly-3-hydroxy valeric acid diol
 VI. Poly-caprolactone diol
 VII. De-polymerized cellulose
 VIII. De-polymerized cellulose acetate is used as a co-condensible diol compound.

17. A material in accordance with claim 16, wherein the polyester diols on the basis of II, IV and V are produced by transesterification of higher-molecular polyesters with ethylene glycol, diethylene glycol and triethylene glycol with simultaneous cleavage into a plurality of macro-diols having a mean molecular weight between $M_n$ 500 and 10000.

18. A material in accordance with claim 17, wherein a diisocyanate is selected from the group consisting of:
 1. 5-isocyanato-1-(isocyanatomethyl)-1,3,3-trimethyl-cyclohexane (isophorone diisocyanate) (IDPI)
 2. 1,3-bis(1-isocyanato-1-methyl)-benzene (TMXDI)
 3. Hexamathylene diisocyanate (HDI)
 4. 2,2,4-trimethyl-hexamethylene diisocyanate (THDI)

19. A material in accordance with claim 18, wherein condensation of the compounds occurs in a solution in a mixture of dioxane/dimethylformamide with a mixing ratio between 1:1 to 20:1 at a temperature between about 40° C. and about 100° C.

20. A material in accordance with claim 19, wherein isolation of the polymers is accomplished by precipitation in water.

21. A material in accordance with claim 20 wherein purification is accomplished by repeated dissolution of the polymer and precipitation in water.

22. A material in accordance with claim 21, wherein said polymer is represented by the formula:

[structure of polymer formula]

where $x \geq 1$, $y \leq 1000$ and $1 \leq n \leq 50$.